US007366563B2

(12) United States Patent
Kleen et al.

(10) Patent No.: US 7,366,563 B2
(45) Date of Patent: *Apr. 29, 2008

(54) CATHETER DEVICE

(75) Inventors: Martin Kleen, Neunkirchen (DE);
Marcus Pfister, Erlangen (DE);
Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 334 days.

This patent is subject to a terminal disclaimer.

(21) Appl. No.: 11/012,971

(22) Filed: Dec. 14, 2004

(65) Prior Publication Data

US 2005/0165303 A1 Jul. 28, 2005

(30) Foreign Application Priority Data

Dec. 15, 2003 (DE) ............... 103 58 735

(51) Int. Cl.
*A61B 5/05* (2006.01)
(52) U.S. Cl. ...................... 600/424; 600/476
(58) Field of Classification Search ............... 600/407, 600/424, 476; 606/15, 17; 607/122
See application file for complete search history.

(56) References Cited

U.S. PATENT DOCUMENTS 5,217,456 A * 6/1993 Narciso, Jr. ................. 606/15
6,171,303 B1 * 1/2001 Ben-Haim et al. ............ 606/15
2001/0031912 A1 10/2001 Adler
2002/0049375 A1 4/2002 Stommer et al.
2005/0203420 A1 * 9/2005 Kleen et al. ................. 600/476

FOREIGN PATENT DOCUMENTS

EP 0 776 176 B1 6/1997
EP 1 078 644 A1 2/2001

* cited by examiner

*Primary Examiner*—Eric F. Winakur
*Assistant Examiner*—Michael Rozanski

(57) ABSTRACT

Catheter device for insertion into an area being examined, in particular into a vessel or cavity-containing organ in the body of a person or animal, wherein in the area of the catheter tip a device (3) is provided for emitting excitation light for light-optically exciting an area being examined surrounding the catheter tip, furthermore a device (3) is provided for collecting response light emitted, owing to excitation, from the area being examined, and furthermore a position sensor (13, 24, 27) is provided enabling the catheter tip's spatial position and/or orientation to be registered in a system of coordinates of a position-registering system (7, 14).

15 Claims, 2 Drawing Sheets

CATHETER DEVICE

CROSS REFERENCE TO RELATED APPLICATIONS

This application claims priority to the German application No. 10358735.7, filed Dec. 15, 2003 which is incorporated by reference herein in its entirety.

FIELD OF INVENTION

The invention relates to a catheter device comprising a catheter, in particular an intravascular catheter, for insertion into an area being examined, in particular into a vessel or cavity-containing organ in the body of a person or animal.

BACKGROUND OF INVENTION

Fluorescent metabolic substances are known from the field of biotechnology which either become concentrated exclusively in certain regions such as, for example, tumors, inflammations, and other specific focuses of a disease, thus being present only locally, or are distributed throughout the body but are activated in terms of their fluorescent property exclusively in certain regions as a result of, for instance, enzyme activity that is peculiar to a tumor. Owing to their fluorescent property, said substances can be employed as markers or marking substances so that a specific, for example already pathological area can be marked or, as the case may be, can be registered at all. A region fluorescently marked in this way is detected by irradiating said region with light of a specific excitation wavelength of the fluorochrome then detecting the emitted light in the corresponding emission wavelength of the fluorogen.

SUMMARY OF INVENTION

So that reasonable use can be made of the diagnostic information content of fluorescent markers of this type it would have to be possible to register said markers as non-invasively as possible on site and furthermore in a manner which, on the one hand, will supply a sufficiently informative and hence diagnostically valuable image representation of the marked area and, on the other hand, will also allow the spatial position of the marked area being examined to be identified with sufficient accuracy.

It is therefore an object of the invention to disclose a method that will permit imaging in a way that is simple and also comfortable for the patient and at the same time will allow the imaging site to be precisely localized.

This object is achieved by the claims.

To implement the minimally invasive examinations, according to the invention a catheter device is provided, in the form in particular of an intravascular catheter, which can preferably be applied in connection with cardiovascular disorders such as "vulnerable plaque". Via the exciter-light emitting device provided according to the invention on its tip, said catheter offers the possibility of exciting a fluorochrome, which is to say the fluorescent marker, possibly present in the area being examined, be this a substance naturally present in the body, which is to say an endogenous substance that may possibly only be activated in the area where the examination is being conducted through relevant enzyme activity, or be this a selectively added fluorescent agent. In the case of an examination of "vulnerable plaque", the fluorescent substance would accumulate in the plaque area: the more aggressive the plaque is, the more there will be of the accumulated substance and the more clearly it will be detectable. Apart from the excitation device, there is also a device for collecting response light emitted, owing to excitation, from the area being examined. The fluorescent effect will occur when the fluorochrome is excited at the corresponding substance-dependent wavelength to which the excitation light needs to have been set, meaning that said fluorochrome will emit response light due to excitation, which light is registered according to the invention via the light-collecting device. Said light is to practical effect passed to a control device, being external to the catheter and communicating therewith, which can produce corresponding images therefrom and output them. A position-registering or orientation-registering device is furthermore provided according to the invention enabling the catheter tip's position/orientation to be registered in a system of coordinates belonging to the position-registering system. This means that the catheter tip can be precisely localized at any time and in any position and hence also that exact spatial coordinates can be specified for any recorded image so that the location of an area possibly requiring intensive therapy is known precisely.

Overall, the device according to the invention thus on the one hand allows a minimally invasive intervention owing to its catheter embodiment; on the other hand, both excitation and the recording of diagnostically relevant responses due to said excitation as well as, simultaneously, the precise registering of spatial coordinates can all be carried out using one and the same device, namely the catheter according to the invention. This accordingly enables physicians to produce, in a manner comfortable for the patient, image recordings based on fluorescent optical excitation which are highly informative and allow precise spatial localizing.

To furnish physicians with a diagnostically even more informative image representation, a practical embodiment of the invention provides for the provision of a control device which controls both image recording, and hence exciting of the fluorochrome, and the generation of images by means of image signals produced based on the response light, which device is embodied for reconstructing, by means of the recorded two-dimensional images, a three-dimensional image of the area being examined. The image recording supplies a multiplicity of individual two-dimensional images of the area being examined. Although physicians can indeed derive plenty of diagnostically relevant information even from said two-dimensional images, they will obtain an even better impression of the area being examined if presented with a three-dimensional reconstructed image of the area being examined which has been produced, as provided according to the invention, via the control device from a multiplicity of individual recorded two-dimensional images. Their orientation within the area being examined, a vessel, say, will be facilitated thereby and the true three-dimensional extent of anatomical structures and pathological processes will be presented to them in a visually readily perceptible manner. This is enabled by the fact that, as described, the integration of the position sensor makes it possible, using the position-registering system, to obtain information about the catheter's position and orientation by means of which position data can be registered for each two-dimensional fluorescent image that is to be or has been recorded and can be assigned to the image.

The position and orientation of each recorded image in the system of coordinates of the position-registering system are thus known. The mutually relative position of two cross-sectional images is furthermore hence also known so that a three-dimensional volume image representing the volume being examined in its true geometry and extent can be generated thereby based on spatial information about the individual cross-sectional images. A volume image showing the object being examined—either after or, using the fluorescent images recorded so far, during the examination—is therefore displayed to physicians in its actual form on a suitable monitor, so that they can recognize the true three-dimensional extent of the anatomical structures being examined as well as any possibly present pathological processes. It is thus possible to produce, as described, say three-dimensional visualizations of vascular pathologies such as, for instance, "vulnerable plaque" or other pathological changes in cavity-containing organs that can be marked using fluorescence technology, and to identify, qualify, and quantify said changes, with the volume presented showing the actual intracorporal conditions. For physicians this accordingly means a significant gain in diagnostically relevant information.

So that the position and spatial orientation of the position sensor, hence of the catheter tip, and hence of the recorded two-dimensional fluorescent images can be determined as precisely as possible in space or, as the case may be, in the system of coordinates of the position-registering system, it is of practical advantage for the position-registering system to determine the sensor's position by means of position data for six degrees of freedom. For each position, six individual sets of position data are therefore determined describing the positions in the x, y, and z direction of the position-registering system's system of coordinates as well as any twisting or tilting that may be present around one of these axes as the additional three sets of position data.

The control device can here be embodied for controlling the operation of the image-recording process as a function of the catheter tip's registered position and/or orientation. That means there is no continuous image recording but, instead, image recording that is triggered via the position data or orientation data. The control device for controlling the operation of the image-recording process can to practical advantage, in particular for reducing the volume of data, be embodied as a function of a registered change in position and/or orientation along at least one degree of freedom. That means that image recording will only take place if the catheter's position/orientation has changed owing to movement. A certain travel increment by the extent of which the catheter tip is to be moved for triggering image recording can conceivably be defined for this for each degree of freedom. Image recording can of course also be triggered based on a change in two or more degrees of freedom. For reconstructing the volume image, two-dimensional images will thus only be recorded if this is actually necessary. The volume of data can therefore be kept relatively small, with even continuous image recording nevertheless taking place when required with simultaneous visualization of the fluorescent images. Physicians have in any event complete freedom of action in how they move the catheter. They can stop the catheter at any time or even move it back since these conditions are clearly recognized via the operational control on the basis of the position-registering system's information describing the incremental movement.

It can furthermore be provided for the control device to be embodied for the merging, with position and/or orientation precision, of a recorded two-dimensional image with a data record, preferably a 3D data record of the area being examined, that was recorded using an external imaging examination modality. Overlaying of the fluorescent image with another image is therefore possible according to the invention. This merely requires registering of the individual images, which will, however, only be possible if the system of coordinates of the position-registering fluorescence system and the system of coordinates of the external examination modality are known: if, therefore, common imaging specifications can be found. Registering based on, for instance, anatomical landmarks present in both data records is also conceivable. Physicians are therefore given the possibility of merging one or more two-dimensional fluorescent images as well as, of course, the three-dimensionally reconstructed fluorescent volume image into, for example, a volume image obtained using a computer tomography system, magnetic resonance system, or ultrasound system. It is, however, in any event necessary, as described, to register the 2D or 3D fluorescent-image data having the morphological data of the data record of the external examination modality.

A specific embodiment of the catheter according to the invention provides for the device for supplying excitation light to include a light conductor ducted inside the catheter up to the catheter tip. Said light conductor is coupled at its rear, extracorporal end to a suitable light source emitting light of the required excitation wavelength. Said light is decoupled on the catheter tip side. The device for collecting the response light can likewise be implemented in the form of a light conductor ducted inside the catheter up to the catheter tip, with the response light being coupled into said light conductor and being passed at the extracorporal end to the control device with, where applicable, a further optical processing device being connected intermediately, with the control device generating the two-dimensional image (and therefrom, where applicable, the three-dimensional image) on the basis of said response light.

Albeit two separate light conductors can be provided for emitting the excitation light and for collecting the response light, a practical embodiment of the invention provides for the provision of a single light conductor for ducting both said excitation light and said response light.

An alternative to using a light conductor for collecting the response light provides for the provision of one or more light sensors located therefor on the catheter tip side, the output signals of which sensors are conveyed over at least one signal lead ducted inside the catheter. Said light sensors likewise collect the response light and convey the response-light information in the form of electrical signals to the control device or, where applicable, to an intermediately connected processing device. The light sensors, preferably several of which are arranged in a distributed manner in the form of an array so that a spatial resolution can also be extracted from the distribution of the signals over the surface of the array, can of course also be provided in addition to the light conductor collecting the response light.

A section that is transparent for the exiting and the entering light is in any event provided on the catheter tip side for decoupling the light and, where applicable, also for coupling it. Said section can be a transparent part of the catheter cover of whatever geometric design or shape.

A particularly practical development of the concept underlying the invention provides for image recording's being triggerable via a triggering device, in particular via an ECG, registering the movement of an organ or such like adjacent to the area being examined or of the area itself being examined. According to this embodiment of the invention external triggering takes place—where applicable additionally to triggering via the position-registering system's information—that will enable the two-dimensional fluorescent images to be recorded for example exclusively during a specific movement phase so that only cophasal fluorescent images will be used for possibly ensuing 3D construction and so that a volume image registered during a very specific movement phase of the area being examined will be obtained. Triggering based on an ECG or triggering by means of a device that registers respiratory movement are conceivable, for instance. It will then be possible, for instance, to record fluorescent images only during a specific respiratory phase or only during a specific cardiac cycle phase and only to use images registered during a specific respiratory or cardiac cycle phase for volume reconstruction.

BRIEF DESCRIPTION OF THE DRAWINGS

Further advantages, features, and specifics of the invention will emerge from the exemplary embodiment described below and with the aid of the drawing.

DETAILED DESCRIPTION OF INVENTION

Figure 1:
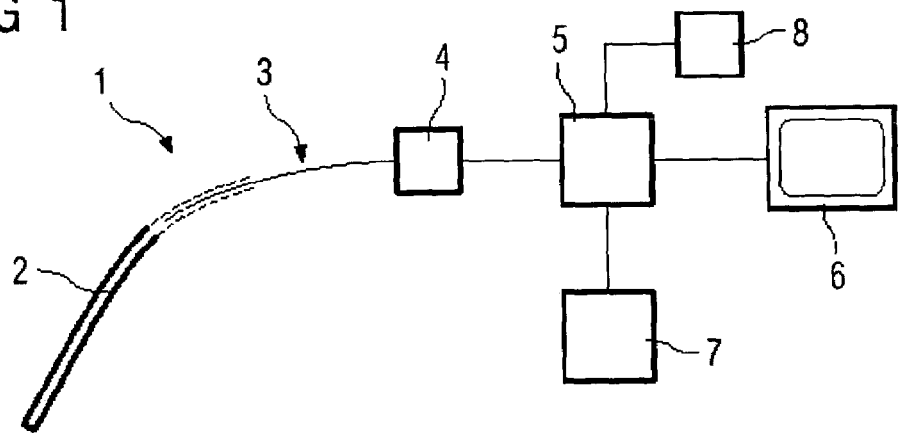
FIG. 1 is a schematic sketch depicting a catheter device according to the invention.

In a schematic sketch, FIG. 1 shows the principal components of a catheter device 1 according to the invention comprising a catheter 2 according to the invention having a device 3 for supplying excitation light emitted on the catheter tip side and for collecting response light emitted due to excitation on the side of the area being examined. Said device 3, dealt with in more detail below, communicates with a device 4 which, depending on the particular embodiment, serves to supply the excitation light and, where applicable, also to receive and process the response light or, as the case may be, corresponding electrical signals of light-sensitive sensors. Provided centrally is a control device 5 which controls all the functions of the catheter device including, for instance, supplying the excitation light and collecting the response light as well as, in particular, processing the response light for generating two-dimensional fluorescent images which can be fed out on a monitor 6, whether as a two-dimensional image or as a three-dimensional reconstructed image. The control device 5 is embodied for reconstructing a three-dimensional volume image based on the two-dimensional fluorescent images.

Further provided is a position-registering system 7 by means of which the catheter tip's position and/or orientation can be registered in a system of coordinates of said position-registering system 7. The corresponding set of spatial coordinates can therefore be registered at any time and for any position/orientation. Information can consequently also be registered in this regard for any image and assigned thereto. This will enable simple reconstruction of a volume image once all spatial coordinates are known.

Further provided in the form of, for instance, an ECG is a triggering device 8 which, like the position-registering system 7, communicates with the control device 5. The movement of the heart, for instance, can be registered via this if the catheter 2 is ducted into an area close to the heart and is also moved synchronously therewith in order thereby, for example, to trigger image recording only during specific cardiac cycle phases and such like registered via the ECG.

Figure 2:
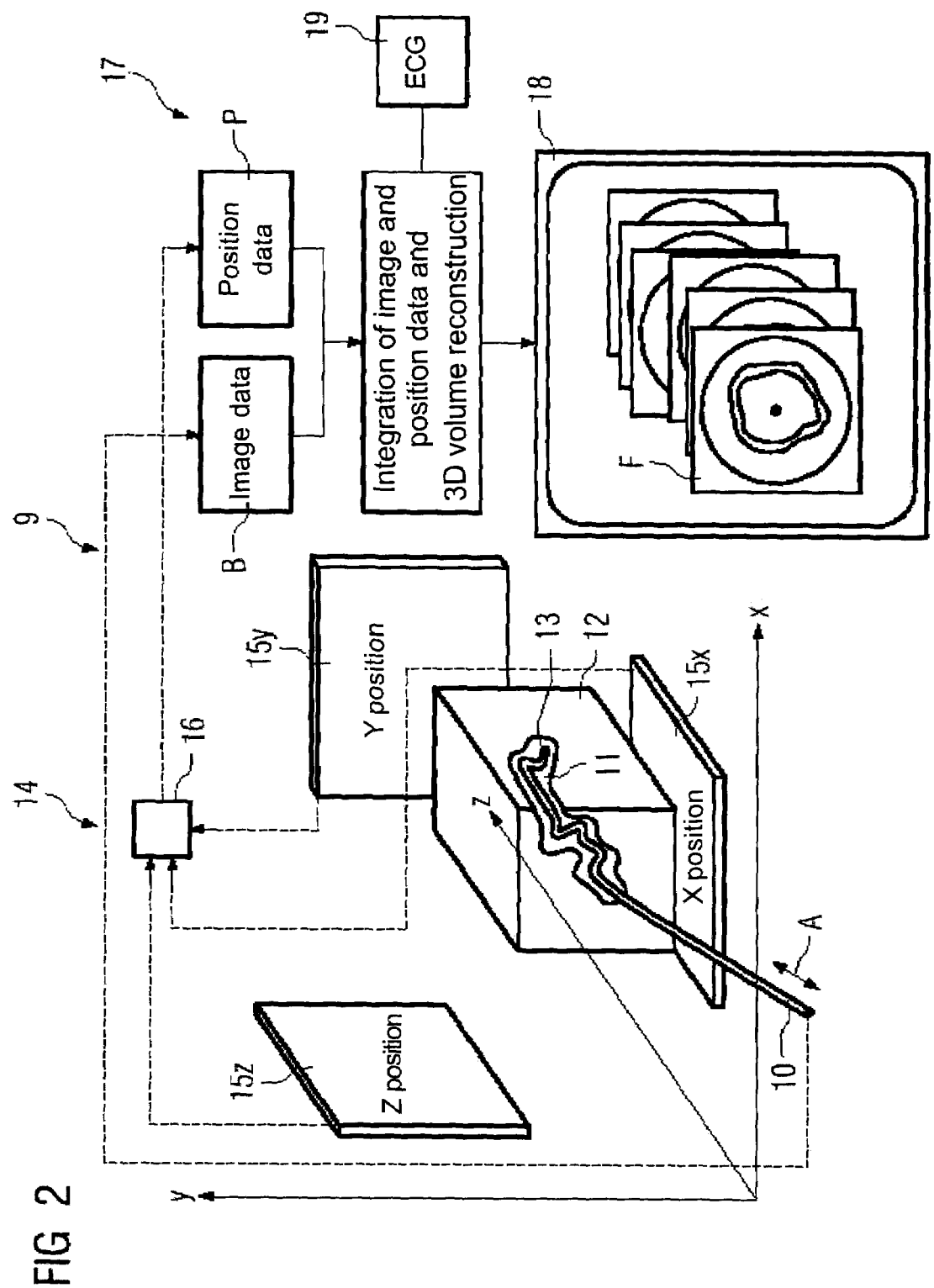
FIG. 2 is a detailed schematic representation of a catheter device according to the invention.

FIG. 2 shows a catheter device 9 according to the invention in greater detail. This contains the already described catheter 10 inserted by the physician for example manually into a vessel 11 of an object being examined 12. On said catheter's tip is a position sensor 13 embodied as an electromagnetic sensor and serving to register the position and orientation in the system of coordinates of the position-registering system 14, represented by means of the coordinate axes x, y, and z. In the figure shown the position-registering system 14 has for this purpose three external receive coils $15x$, $15y$, $15z$ via which are registered, on the one hand, the respective position of the position sensor 13 in the x, y, and z direction and, on the other hand, the respective rotations about said axes which the position sensor 13 describes. A total of six sets of position data are therefore registered for one sensor position.

The position data is accordingly determined in a control device 16 of the position-registering system and passed as position data P to the control device 17, which simultaneously performs all data and signal evaluations.

As already described with reference to FIG. 1, light is radiated via the catheter 10 into the area being examined, this taking place in, for example, a rotating manner so that two-dimensional circular recordings are made in the form of two-dimensional fluorescent images F. It is also possible to operate with a fixed direction of radiation oriented in the longitudinal direction of the catheter; the light is therefore radiated directly by the catheter tip in a forward direction. To produce the fluorescent images, the response light resulting from the light's inward radiation is received in the catheter tip, decoupled via the catheter 2, and passed to the control device 17, where the information is processed into two-dimensional fluorescent-image data B receiving the image information.

The response light originates from fluorescent substances which accumulate in a pathologically relevant section of the area being examined and which are excited to emit light by the excitation light to which they are exposed. Said response light is collected as described as it will supply diagnostically relevant information from the area being examined on the basis of which information the described generation of image data takes place.

As indicated by the double arrow A, the catheter is moved relative to the vessel 11. Each movement being accompanied by a change in the position sensor's position, any change in position or orientation, no matter how slight, can be registered via the position-registering system. It is of practical advantage for the image-recording or processing process to be triggered via this information in such a way that, for example, a two-dimensional image will only be recorded if the position sensor has been moved by the extent of a predefined travel increment within or, as the case may be, by the extent at least of one of the cited six degrees of freedom, which can be clearly registered via the position-registering system. It can thereby be precluded that images will be continuously recorded or, as the case may be, subsequently processed into a three-dimensional reconstructed image when the catheter is static and that there will consequently be an excessive volume of data. It is also conceivable to select, via this information, from the plethora of continuously recorded fluorescent images specific fluorescent images to be used for 3D reconstruction. The mode of operation is variable.

In any event, the image data B and the position data P present in the control device 17 are "married" there, which is to say that each two-dimensional image data record is assigned the respective plethora of position data. The three-dimensional volume reconstruction is then carried out in said control device 17 using said position data and said image data. Its being known from the position data present for each fluorescent image F how an image is positioned or, as the case may be, oriented with respect to a second image, it is possible to mutually relate the fluorescent images in such a way that the volume image will reproduce the actual geometric or, as the case may be, anatomical relationships of the vessel 11. The volume image is fed out on the monitor 18. Albeit FIG. 2 show s the fluorescent images F in a mutually displaced arrangement, it should be noted that the fluorescent images can of course also be tilted in relation to each other depending on the actual shape of the vessel.

As further shown in FIG. 2, it is possible to perform triggering via an external triggering means, via in this case the ECG 19 recorded in parallel, in such a way that only 2D image data recorded in the same phase will be used for 3D volume reconstruction. Alongside said triggering relating to image processing, it is of course also possible to trigger image recording itself via said external triggering means in conjunction with the data, supplied by the position-registering system 14, relating to the travel increment passed. Image recording would in this case only take place when the travel increment has been passed and the respective triggering phase attained.

The control device is further embodied for merging the recorded 2D fluorescent images or the reconstructed volume with a data record supplied by another examination modality. That means it is possible to link in, for example, fluorescent images recorded with the exact position in a magnetic resonance volume data record or to link in the reconstructed fluorescent volume. Necessary registering of the data records can be carried out via, for example, anatomical landmarks, which is to say via specific prominent anatomical areas of the recorded image. A joint presentation is also possible alongside image merging.

Figure 3:
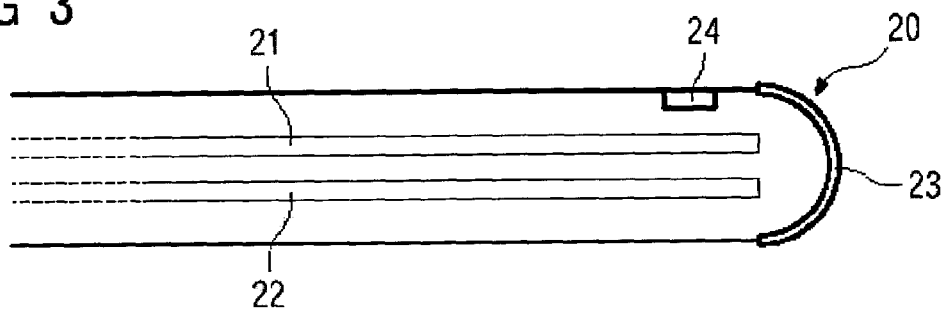
FIG. 3 is a schematic view of the catheter tip of a first embodiment.

FIG. 3 shows a catheter tip 20 of a specific first catheter implementation. What is shown are a first light conductor 21 via which the excitation light is ducted and a second light conductor 22 into which the response light is coupled and ducted away. The catheter tip has a transparent cover 23 through which the excitation light is directly emitted or, as the case may be, the response light is coupled. The position sensor 24 is also shown.

Figure 4:
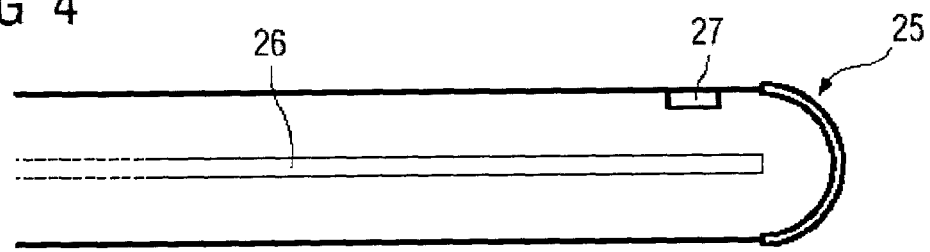
FIG. 4 is a schematic view of the catheter tip of a second embodiment.

FIG. 4 shows a further catheter tip 25 of a further catheter implementation. Only a single light conductor 26 is provided here via which both the excitation light is ducted and the response light collected. A position sensor 27 is also integrated here on the catheter tip side.

Figure 5:
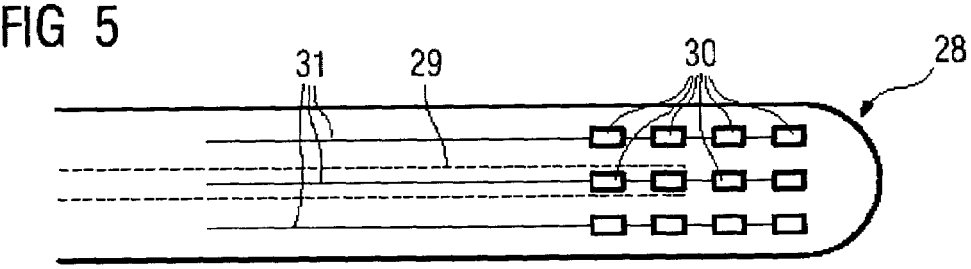
FIG. 5 is a schematic view of the catheter tip of a third embodiment.

FIG. 5, finally, is an exterior view of a further catheter tip 28. Provided internally is a light conductor 29 serving to duct the excitation light radiated in the exemplary embodiment shown for example outward in a circular manner perpendicular to the longitudinal axis of the catheter, which is to say the light rotates so that circular recordings are possible in the area being examined. On the other hand, in the embodiments described the response light is not, however, collected via a light-conducting fiber but, instead, via light sensors 30 provided preferably outside the catheter and arranged over a relatively large area in the form of an array and preferably distributed around the entire catheter circumference. The light sensors are connected to a downstream signal-collecting device via suitable signal leads 31. It is possible via this quasi contiguous planar sensor arrangement on the one hand to precisely register the local distribution of the response light and, on the other hand, thereby also to obtain position information, as each sensor occupies a specific position and produces separate sensor signals.

The invention claim is:

1. A catheter device for fluorescence or autofluorescence medical examination, comprising:
   a catheter having a catheter tip for inserting into an examination area;
   an excitation device arranged adjacent to the catheter tip for emitting excitation light adapted to light-optically exciting an investigation area adjacent to the catheter tip to produce fluorescent or autofluorescent response light;
   a receiver device for receiving said response light emitted from the investigation area as consequence of the light-optically excitation of the investigation area;
   a position sensor for detecting a spatial position or an orientation of the catheter tip relative to a coordinate system of a position detecting device; and
   an image recording control device adapted to:
      control the light-optically exciting of the investigation area;
      control a generation of fluorescent or autofluorescent two-dimensional medical images using image signals, the image signals generated using the response light;
      reconstruct a three-dimensional image of the investigation area using the two-dimensional medical images and the spatial position or the orientation respectively of the catheter tip; and
      control a recording of at least one of the two-dimensional medical images based on a detected change of position or change of orientation respectively relative to a previous position or orientation respectively of the moving catheter tip for reducing an image data volume to be recorded, wherein the detected change of position or orientation respectively triggers the recording of the two-dimensional image only if the detected change of position or orientation respectively matches or exceeds a pre-defined travel increment.

2. The catheter device according to claim 1, wherein the travel increment is at least two-dimensional thus having at least two directional components and the recording of the two-dimensional image is only triggered if the detected change of position or orientation respectively matches or exceeds the pre-defined travel increment with regard to at least one of the directional components.

3. The catheter device according to claim 1, wherein the catheter is an intravascular catheter.

4. The catheter device according to claim 1, wherein the examination area is a vessel or a hollow organ of a human or an animal.

5. The catheter device according to claim 1, wherein the coordinate system has six coordinates and the position sensor is adapted to detect the spatial position relative to the six coordinates.

6. The catheter device according to claim 1, wherein the image recording control device is further adapted to merge a recorded two-dimensional image with an image data record recorded by an external imaging examination device, the merging providing for an exact positioning of the recorded two-dimensional image within the image data record.

7. The catheter device according to claim 6, wherein the image data recorded is a three-dimensional image data record of at least part of the examination area.

8. The catheter device according to claim 1, wherein the excitation device includes an optical fiber arranged inside the catheter and directed to the catheter tip.

9. The catheter device according to claim 1, wherein the receiver device includes a further optical fiber arranged inside the catheter and directed up to the catheter tip.

10. The catheter device according to claim 1, wherein the catheter comprises a single optical fiber for ducting the excitation light and registering the response light.

11. The catheter device according to claim 1, further comprising a light collecting device for collecting the response light, the light collecting device including at least one light sensor arranged adjacent to the catheter tip, wherein an output signal of the light sensor is transmitted over at least one signal line arranged inside the catheter.

12. The catheter device according to claim 11, wherein a plurality of light sensors are arranged inside the catheter, the light sensors forming a sensor array.

13. The catheter device according to claim 1, wherein the catheter tip includes a section transparent for the excitation and the response light.

14. The catheter device according to claim 1, further comprising a triggering device for triggering an image recording process of the catheter device using a registered movement of an organ adjacent to the examination area or the investigation area.

15. The catheter device according to claim 14, wherein the triggering device includes an ECG.

* * * * *